United States Patent [19]

Tsunekawa et al.

[11] Patent Number: 4,915,368
[45] Date of Patent: Apr. 10, 1990

[54] METHOD OF AND APPARATUS FOR ARRANGING SHEETS

[75] Inventors: Yuzo Tsunekawa; Yukio Ishida; Tatsuo Shiino, all of Kanagawa, Japan

[73] Assignee: Fuji Photo Film Co., Ltd., Japan

[21] Appl. No.: 153,297

[22] Filed: Feb. 5, 1988

[30] Foreign Application Priority Data

Feb. 6, 1987 [JP] Japan .................... 62-26126

[51] Int. Cl.⁴ ............................................ B65H 39/02
[52] U.S. Cl. ........................................ 270/58; 53/246; 53/520; 53/250; 53/251
[58] Field of Search ............ 270/58, 52; 53/246, 53/520, 251, 250

[56] References Cited

U.S. PATENT DOCUMENTS

| | | | |
|---|---|---|---|
| 3,340,677 | 9/1967 | Luxemborg | 53/250 |
| 4,518,157 | 5/1985 | Stobb | 270/58 |
| 4,616,473 | 12/1986 | Hodges et al. | 53/520 |
| 4,630,428 | 12/1986 | Lesch | 53/246 |

FOREIGN PATENT DOCUMENTS

| | | | |
|---|---|---|---|
| 1308372 | 9/1962 | France | 53/246 |
| 52-21677 | 7/1978 | Japan . | |
| 164356 | 12/1980 | Japan . | |
| 672938 | 5/1952 | United Kingdom | 270/58 |

Primary Examiner—Robert E. Garrett
Assistant Examiner—Therese M. Newholm
Attorney, Agent, or Firm—Sughrue, Mion, Zinn, Macpeak & Seas

[57] ABSTRACT

When arranging a plurality of sheets side by side in predetermined pattern on a sheet receiving member, the sheets are fed to a receiving position one by one, and are picked up one by one by a suction cup on a rotatable arm member. The rotatable arm member is rotated to bring each sheet picked up by the suction cup to a delivery position, and the sheet is placed on the part of the sheet receiving member positioned in the delivery position while the sheet receiving member is moved, in synchronization with rotation of the rotatable arm member, along a predetermined path corresponding to said predetermined pattern so that a new part of the sheet receiving member is brought to the delivery position each time the sheet receiving member is moved. This method is applicable to a process for making chemical analysis slides.

5 Claims, 8 Drawing Sheets

METHOD OF AND APPARATUS FOR ARRANGING SHEETS

FIELD OF THE INVENTION

This invention relates to a method of arranging a plurality of sheets side by side in a predetermined pattern and an apparatus for carrying out the method. More specifically, this invention relates to a method of arranging chemical analysis films side by side in a predetermined pattern on a sheet in assembly of chemical analysis slides for chemical analysis of a sample liquid, and to an apparatus for carrying out the method.

DESCRIPTION OF THE PRIOR ART

There has been put into practice a dry type chemical analysis slide for analyzing a chemical component or material component such as glucose, bilirubin, urea, nitrogen or the like contained in a sample liquid, e.g., a body fluid, by simply depositing a droplet of the sample liquid on the slide. See, for example, Japanese Patent Publication No. 53(1978)-21677 and Japanese Unexamined Patent Publication No. 55(1980)-164356. When analyzing a chemical component or the like in a sample liquid by use of such a chemical analysis slide, a small amount of sample liquid is measured and deposited on the chemical analysis film of the chemical analysis slide, and the chemical analysis slide bearing thereon the sample liquid is incubated for a predetermined time in an incubator, thereby promoting color reaction. Then measuring light containing a wavelength predetermined according to the combination of the component in the sample liquid and the reagent contained in the reagent layer on the chemical analysis film is projected onto the chemical analysis slide and the reflection density of the chemical analysis film is measured.

Figure 8:
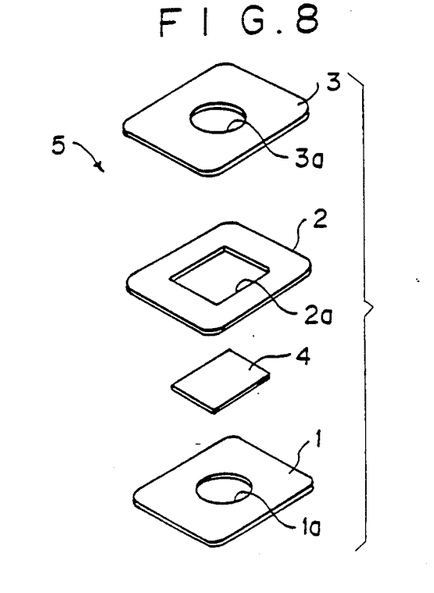
FIG. 8 is an exploded perspective view showing a chemical analysis slide to be assembled by the apparatus.

As shown in FIG. 8, for example, the chemical analysis slide 5 comprises a mount base 1 formed of a rectangular plastic sheet having a reflection density measuring opening 1a through which the reflection density of the chemical analysis film is measured, a mount frame 2 formed of a rectangular plastic sheet having a chemical analysis film holding opening 2a larger than the reflection density measuring opening 1a in size, a chemical analysis film 4 held in the chemical analysis film holding opening 2a, and a mount cover 3 formed of a rectangular plastic sheet having a sample liquid depositing opening 3a through which a sample liquid is deposited on the chemical analysis film 4. The mount base 1, the mount frame 2 and the mount cover 3 are bonded together with the mount frame 2 being sandwiched between the mount base 1 and the mount cover 3 and the chemical analysis film 4 being placed in the chemical analysis film holding opening 2a.

There has been known a method of continuously assembling a plurality of such chemical analysis slides in order to increase assembling efficiency of the slides. In the known method, plastic sheets in continuous lengths are unrolled from respective rolls, and are respectively formed with the reflection density measuring opening 1a, the chemical analysis slide holding opening 2a and the sample liquid depositing opening 3a. The sheets are superposed one on another and bonded together with the chemical analysis films 4 being held in the holding opening 2a, and then the chemical analysis slides are stamped to a predetermined shape from the assembly thus obtained.

When continuously assembling the chemical analysis slides, the chemical analysis films must be placed in the chemical analysis film holding openings in the film. It is preferred that a plurality of the films be placed in the openings at one time from the viewpoint of efficiency. There have been known several methods of and apparatuses for aligning sheets such as the chemical analysis films in a predetermined pattern. However, they are not satisfactory since a complicated structure is required.

SUMMARY OF THE INVENTION

In view of the foregoing observations and description, the primary object of the present invention is to provide a method of and an apparatus for easily arranging sheets such as chemical analysis films side by side in a predetermined pattern.

In one aspect of the present invention, there is provided a method of arranging a plurality of sheets side by side in a predetermined pattern on a sheet receiving member comprising the steps of feeding the sheets to a receiving position one by one, picking up one by one the sheets fed to the receiving position by a suction means on a rotatable arm member, rotating the rotatable arm member to bring each sheet picked up by the suction means to a delivery position, and placing the sheet on the part of the sheet receiving member positioned in the delivery position while moving the sheet receiving member in synchronization with the rotation of the rotatable arm member along a predetermined path corresponding to said predetermined pattern so that a new part of the sheet receiving member is brought to the delivery position each time the sheet receiving member is moved.

In another aspect of the present invention, there is provided an apparatus for arranging a plurality of sheets side by side in a predetermined pattern on a sheet receiving member comprising means for feeding the sheets to a receiving position one by one, a rotatable arm member rotatable about a pivot shaft back and forth between the receiving position and a delivery position, a suction means which is mounted on the rotatable arm member and adapted to pick up the sheets one by one under vacuum force, a flexible suction hose for connecting the suction means to a vacuum source, a support means for movably supporting the sheet receiving member in the delivery position, and a drive means for moving the sheet receiving member in synchronization with the rotation of the rotatable arm member along a predetermined path corresponding to said predetermined pattern so that a new part of the sheet receiving member is brought to the delivery position each time the sheet receiving member is moved.

It is preferred that the suction means be connected to the flexible suction hose by way of a vacuum passage which is formed through the rotatable arm member to extend near the pivot shaft and is connected to the suction hose at the end near the pivot shaft.

DESCRIPTION OF THE PREFERRED EMBODIMENT

Figure 1:
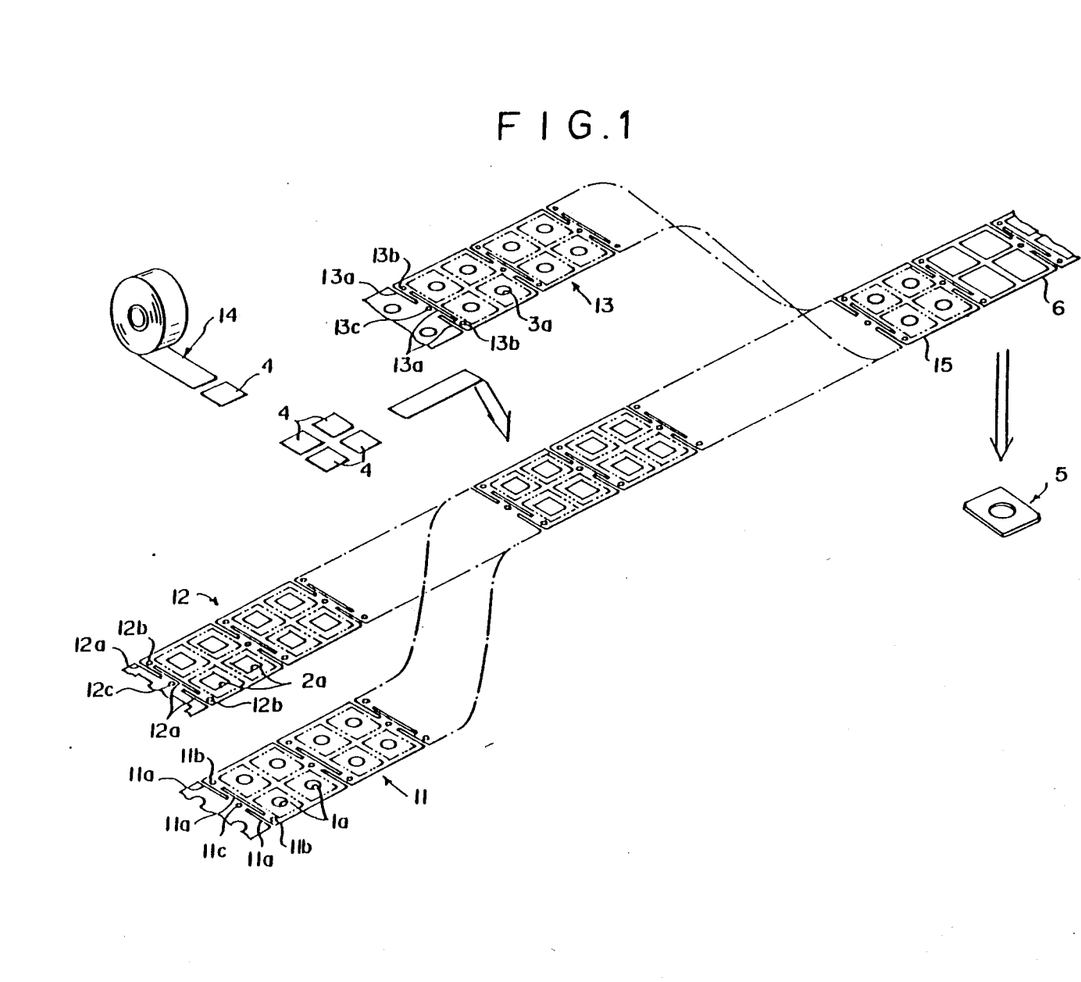
FIG. 1 is a schematic perspective view showing chemical analysis slide assembling steps in which the method and apparatus of the present invention are applied.

In FIG. 1, first, second and third plastic sheets 11, 12 and 13 in continuous lengths for respectively forming mount bases, mount frames and mount covers are supplied from rolls (not shown), for instance. The first plastic sheet 11 is provided with a plurality of openings arranged in two rows extending in the longitudinal direction of the sheet 11 and numbers of columns perpendicular to the rows. The openings are for forming the reflection density measuring openings 1a in finished products described above in conjunction with FIG. 8 as will become apparent later, and accordingly, are indicated at 1a in the drawings and will be referred to as "the reflection density measuring openings 1a", hereinbelow. Similarly, the second and third plastic sheets 12 and 13 are respectively provided with a plurality of openings arranged in two rows extending in the respective longitudinal directions thereof and numbers of columns perpendicular to the rows. The openings are respectively for forming the chemical analysis film holding openings and the sample liquid depositing openings in finished products described above in conjunction with FIG. 8, and accordingly, are indicated at 2a and 3a in the drawings and will be referred to as "the chemical analysis film holding openings 2a" and "the sample liquid depositing openings 3a", hereinbelow. The first to third plastic sheets 11 to 13 are cut along the double dotted chain lines after being bonded together to form individual chemical analysis slides. The plastic sheets 11 to 13 are intermittently conveyed at regular intervals by a conveying means which may be of a feed pin system, for instance. The reflection density measuring openings 1a are divided into groups of four each formed of two adjacent columns, and three transverse slits 11a are formed in the first plastic sheet 11 between each pair of adjacent groups, two of the three slits 11a extending inwardly from opposite edges of the first plastic sheet 11 in alignment with each other and the other slit 11a extending in parallel to the other two slits 11a at the middle of the sheet 11. That is, numbers of sheet segments each for forming four mount bases are linked together with the three slits 11a intervening between each pair of adjacent sheet segments. A pair of locating holes 11b are provided near the edges of the sheet 11 between each pair of adjacent sheet segments and perforations 11c for feeding the film 11 are provided along the longitudinal axis of the sheet 11, one between each pair of adjacent sheet segments. Similarly, the chemical analysis film holding openings 2a are divided into groups of four each formed of two adjacent columns, and three transverse slits 12a are formed in the second plastic sheet 12 between each pair of adjacent groups, two of the three slits 12a extending inwardly from opposite edges of the second plastic sheet 12 in alignment with each other and the other slit 12a extending in parallel to the other two slits 12a at the middle of the sheet 12. That is, numbers of sheet segments each for forming four mount frames are linked together with the three slits 12a intervening between each pair of adjacent sheet segments. A pair of locating holes 12b are provided near the edges of the sheet 12 between each pair of adjacent sheet segments and perforations 12c for feeding the film 12 are provided along the longitudinal axis of the sheet 12, one between each pair of adjacent sheet segments. Similarly, the sample liquid depositing openings 3a are divided into groups of four each formed of two adjacent columns, and three transverse slits 13a are formed in the third plastic sheet 13 between each pair of adjacent groups, two of the three slits 13a extending inwardly from opposite edges of the third plastic sheet 13 in alignment with each other and the other slit 13a extending in parallel to the other two slits 13a at the middle of the sheet 13. That is, numbers of sheet segments each for forming four mount covers are linked together with the three slits 13a intervening between each pair of adjacent sheet segments. A pair of locating holes 13b are provided near the edges of the sheet 13 between each pair of adjacent sheet segments and perforations 13c for feeding the film 13 are provided along the longitudinal axis of the sheet 13, one between each pair of adjacent sheet segments. The chemical analysis films 4 are obtained by cutting a rolled chemical analysis film sheet 14 of a predetermined width in predetermined lengths. The slits 11a, 12a and 13a accommodate difference in position among the sheet segments in the respective plastic sheets as well as stretch of the sheets 11, 12 and 13, and prevent meander of the sheets 11, 12 and 13.

While the first and second plastic sheets 11 and 12 are conveyed, the second plastic sheet 12 is superposed on the first plastic sheet 11 and the reflection density measuring openings 1a in the first plastic sheet 11 are aligned with the chemical analysis film holding openings 2a in the second plastic sheet 12, and then the sheets 11 and 12 are bonded together. More particularly, feed pins are inserted into the perforations 11c and 12c of the first and second plastic sheets 11 and 12 to convey the sheets 11 and 12 in the superposed state. Further, as a result of the insertion of the feed pins into the perforations, the sheets 11 and 12 are substantially aligned with each other. When the sheets 11 and 12 are bonded together, locating pins are inserted into the locating holes 11b and 12b to bring corresponding sheet segments of the respective sheets 11 and 12 in precise alignment with each other, and then the sheets 11 and 12 are bonded together by means of adhesive, ultrasonic welding or the like. Thus a sheet assembly in a continuous length having spaces for accommodating therein chemical analysis films 4 defined by the chemical analysis film holding openings 2a in the second plastic film 12 is formed.

While the sheet assembly is further conveyed by the feed pins, the chemical analysis films 4 are inserted into the spaces defined by the chemical analysis film holding openings 2a by suitable means such as a pick-and-place apparatus. Thereafter, the third plastic sheet 13 is superposed on the sheet assembly on the second plastic sheet side while they are being conveyed, and then they are bonded together. Thus, a sheet assembly 15 in a continuous length having therein the chemical analysis films 4 accommodated in the openings 2a and held therein by the third plastic film 13 is obtained. The sheet assembly 15 is stamped along the double dotted chain line in FIG. 1 to produce a plurality of individual chemical analysis slides 5. Also when the third plastic sheet 13 is bonded to the second plastic sheet and the individual chemical analysis slides 5 are cut out from the sheet assembly 15, locating pins are inserted into the locating holes for precise location of the plastic sheets with respect to each other or to the stamping means. During the steps described above, the slits 11a, 12a and 13a between the sheet segments of the respective plastic sheets 11, 12 and 13 absorb stretch and/or meander of the sheets 11, 12 and 13 to permit precise location of the sheets 11, 12 and 13 by the locating pins. Thus, the openings 1a, 2a and 3a are correctly aligned with each other in the finished products and since none of the sheets 11, 12 and 13 is stretched when the sheets are actually bonded together, warpage is not produced in finished products. The remainder 6 may be cut in suitable lengths and thrown away.

An example of an apparatus for assembling the chemical analysis slides in the manner described above will be described with reference to FIGS. 2 to 7, hereinbelow.

Figure 2:
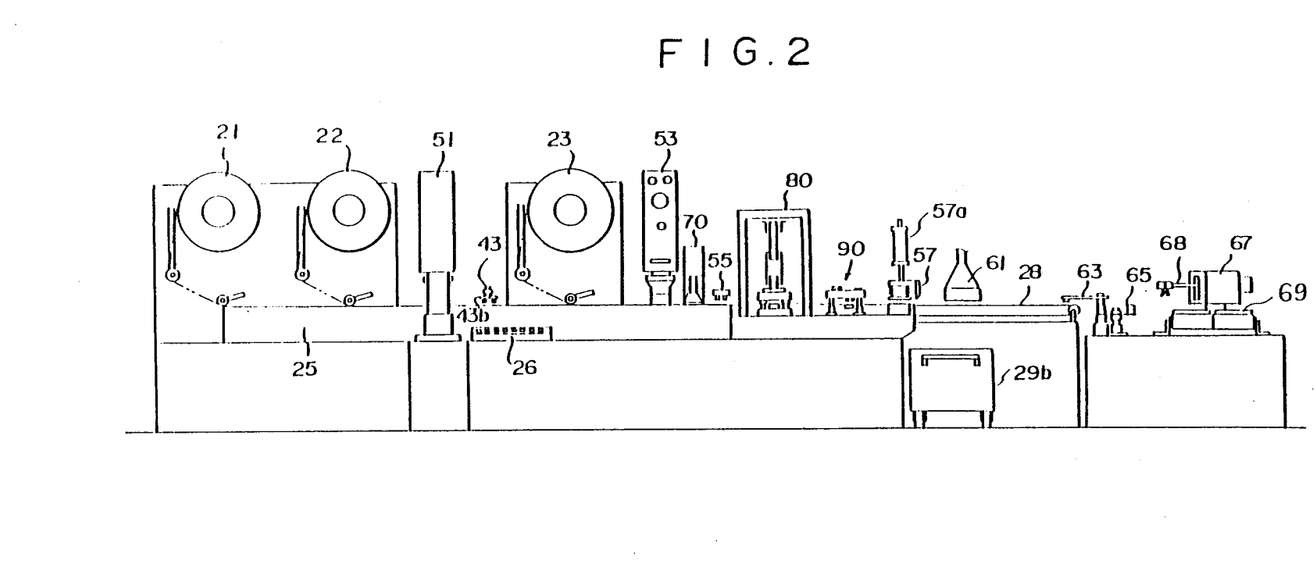
FIG. 2 is a front elevational view of an apparatus for carrying out the assembling steps shown in FIG. 1.

This apparatus has a first conveying passage 25 along which the first to third plastic sheets 11, 12 and 13 are conveyed from the left to the right as seen in FIG. 2. Above the first conveying passage 25, there are disposed first to third sheet supply reels 21, 22 and 23 for respectively feeding the first to third plastic sheets 11 to 13 to the first conveying passage 25. A first ultrasonic welder 51 is provided between the second and third reels 22 and 23. The second plastic sheet 12 fed to the first conveying passage 25 from the second sheet supply reel 22 is superposed on the first plastic sheet 11 fed to the first conveying passage 25 from the first sheet supply reel 21, and aligned sheet segments of the first and second plastic sheets 11 and 12 are welded together by the first ultrasonic welder 51.

Figure 3:
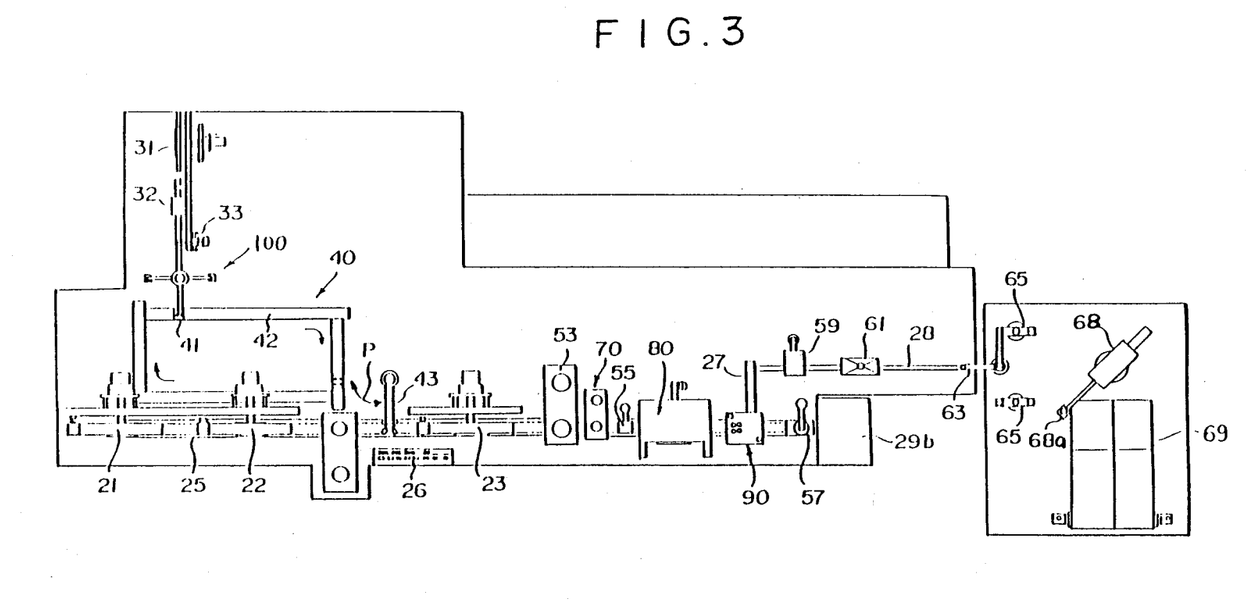
FIG. 3 is a plan view of the apparatus shown in FIG. 2.

Subsequently, the chemical analysis films 4 are inserted into the chemical analysis film holding openings 2a of the second plastic sheet 12. This insertion of the films 4 is accomplished simultaneously for the four chemical analysis film holding openings 2a in each sheet segment and will be described in detail with reference to FIGS. 4A and 4B. The chemical analysis film sheet 14 is rolled around a fourth reel 31 (FIG. 3). After being unrolled from the fourth reel 31, the chemical analysis film sheet 14 is inspected by a sample inspection device 32 (This inspection is for detecting substandard portions which have been marked during production of the film sheet 14.) and then cut in predetermined lengths by a cutter 33 to form chemical analysis films 14 of a predetermined size. The chemical analysis films 4 are placed on a pallet 41 of a pallet conveying section 40 by a high speed transfer means 100 in accordance with an embodiment of the present invention.

Figure 4A:
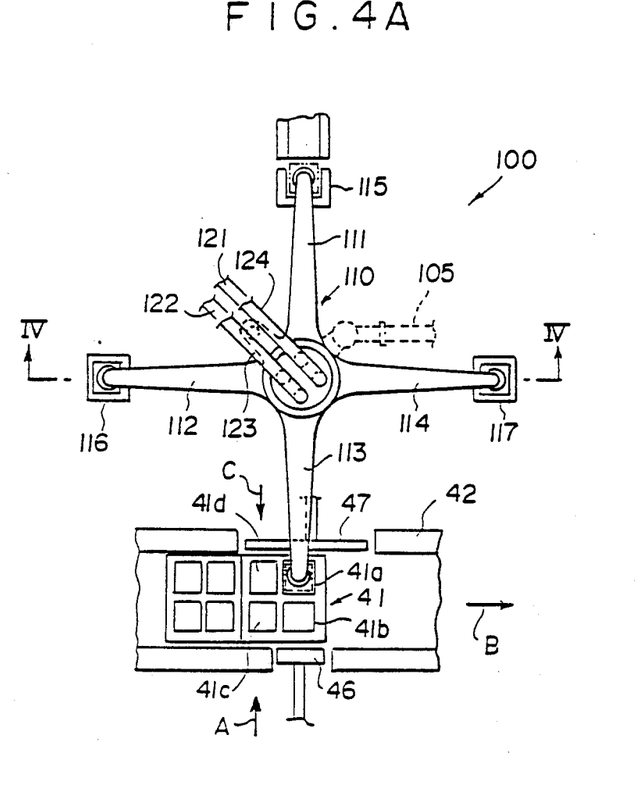
FIG. 4A is an enlarged plan view showing in more detail an embodiment of the present invention employed in the apparatus as the high speed transfer means.
Figure 4B:
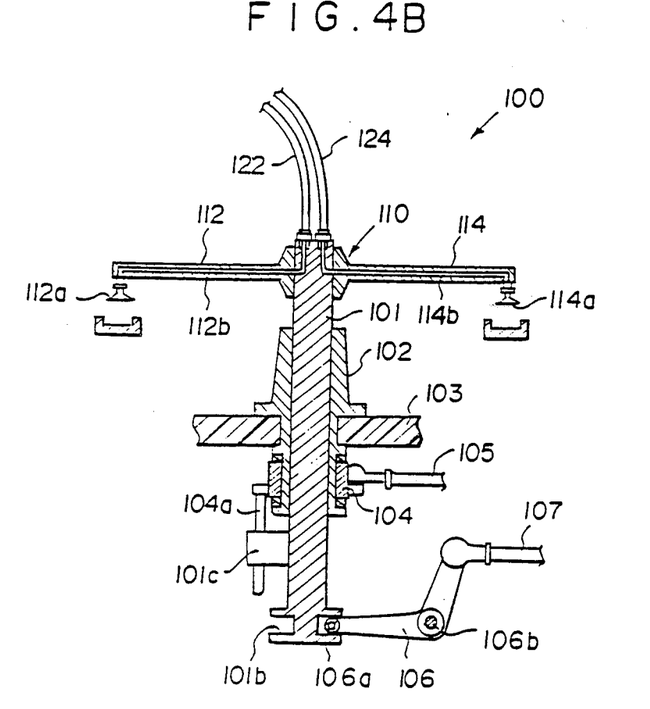
FIG. 4B is a cross-sectional view taken along line IV—IV in FIG. 4A.

As shown in detail in FIGS. 4A and 4B, the high speed transfer means 100 has a pivot shaft 101 which is supported for rotation and for up-and-down sliding motion by a bearing 102 fixed to a base 103. To the upper end of the pivot shaft 101 is fixedly mounted a rotatable member 110 having four (first to fourth) arms 111 to 114 radially extending horizontally from the upper end of the pivot shaft 101 at intervals of 90°. The arms 111 to 114 are respectively provided with suction cups 111a to 114a on the lower surfaces of the free ends thereof. Four suction hoses 121 to 124 extending from a vacuum source 120 (FIG. 5) are respectively connected to vacuum passages 11b to 114b (only 112b and 114b are shown) open in the top surface of the pivot shaft 101. The vacuum passages 111b to 114b are formed to extend respectively through the arms 111 to 114 to communicate the suction cups 111a to 114a with the suction hoses 121 to 124. The suction hoses 121 to 124 are made of flexible material. An annular groove 101b is formed on a lower end portion of the pivot shaft 101 to extend in the circumferential direction of the shaft 101. A free end 106a of a vertical motion link 106 is fit into the groove 101b. The vertical motion link 106 is driven by a first rod 107 to rotate about a support shaft 106b, whereby the free end 106a of the link 106 is moved up and down causing the pivot shaft 101 to move up and down therewith. A connecting member 104 is fit on a lower end portion of the bearing 102 to be rotatable relative to the bearing 102. A pin 104a extends downward from the connecting member 104 and extends for vertical sliding motion through a support 101c fixed to the pivot shaft 101. A second rod 105 is connected to the connecting member 104 and when the connecting member 104 is rotated by the second rod 105, the pivot shaft 101 is rotated by way of the pin 104a and the support 101c.

As shown in FIG. 4A, first to third tables 115 to 117 and a pallet 41 are provided at intervals of 90° along a circle along which the suction cups 111a to 114a are moved as seen from above when the rotatable member 110 is rotated. The first table 115 and the pallet 41 are diametrically opposed to each other, and the second and third tables 116 and 117 are diametrically opposed to each other. When the rotatable member 110 is moved downward driven by the first rod 107, the suction cups 111a and 112a on the first and second arms 111 and 112 respectively pick up chemical analysis films 4 from the first table 115 and the second table 116. Thereafter, the rotatable member 110 is moved upward while being counterclockwisely rotated by 90°, thereby bringing the films 4 picked up by the suction cups 111a and 112a respectively above the second table 116 and the pallet 41, and then the rotatable member 110 is moved downward and the suction cups 111a and 112a release the films 4 onto the second table 116 and the pallet 41. At the same time, the suction cups 113a and 114a on the third and fourth arms 113 and 114 pick up a film 4 from the third table 117 and the film 4 fed to the first table 115. Thereafter, the rotatable member 110 is moved upward while clockwisely rotated by 90°, thereby bringing the film 4 on the suction cups 113a and 114a respectively above the pallet 41 and the third table 117, and then the rotatable member 110 is moved downward and the suction cups 113a and 114a release the films 4 onto the pallet 41 and the third table 117. By repeating the cycle described above, the films 4 fed to the first table 115 are transferred to the pallet 41 one by one. The pallet 41 is conveyed along a conveying passage 42 of a pallet conveying section 40 in the direction shown by arrow B, and at the same time, can be moved in the transverse direction of the conveying passage 42 by first and second drive means 46 and 47 as shown by arrows A and C. The pallet 41 is moved in synchronization with the rotatable member 110 in the following manner. In the state shown in FIG. 4A, a first film receiving portion 41a of the pallet 41 is in the film delivery position in which it is aligned with the suction cup 113a on the third arm 113, and the film 4 held by the suction cup 113a is placed on the first film receiving portion 41a. Thereafter, the first drive means 46 pushes the pallet 41 to move a second film receiving portion 41b to the film delivery position in which it is aligned with the suction cup 112a on the second arm 112 and the film 4 held by the suction cup 112a is placed on the second film receiving portion 41b. The pallet 41 is subsequently moved along the passage 42 in the direction of arrow B to bring a third film receiving portion 41c to the film delivery position. After the third film receiving portion 41c receives the film 4, the pallet 41 is pushed by the second drive means 47 in the direction of arrow C to bring a fourth film receiving portion 41d to the film delivery position. In this manner, the films 4 transferred to the film delivery position one by one each time the rotatable member 110 is rotated are arranged on the pallet 41 in a predetermined pattern.

Since the rotatable member 110 may only be rotated back and forth by 90°, and such movement can be accommodated by flexibility of the suction hoses 121 and 124. This is advantageous in that the rotatable member 110 which is rotated back and forth and the suction source 120 which is stationary can be connected without using a complicated joint member such as a rotary joint. Any film 4 having a substandard portion detected by the sample inspection device 32 is removed and not delivered to the pallet 41. This is accomplished, for instance, by interrupting the suction force to the suction cup while the rotatable member 110 is being rotated or by hitting the film against an abutment member which is selectively projected into and retracted from the path of the film while the rotatable member 110 is being rotated.

Figure 4C:
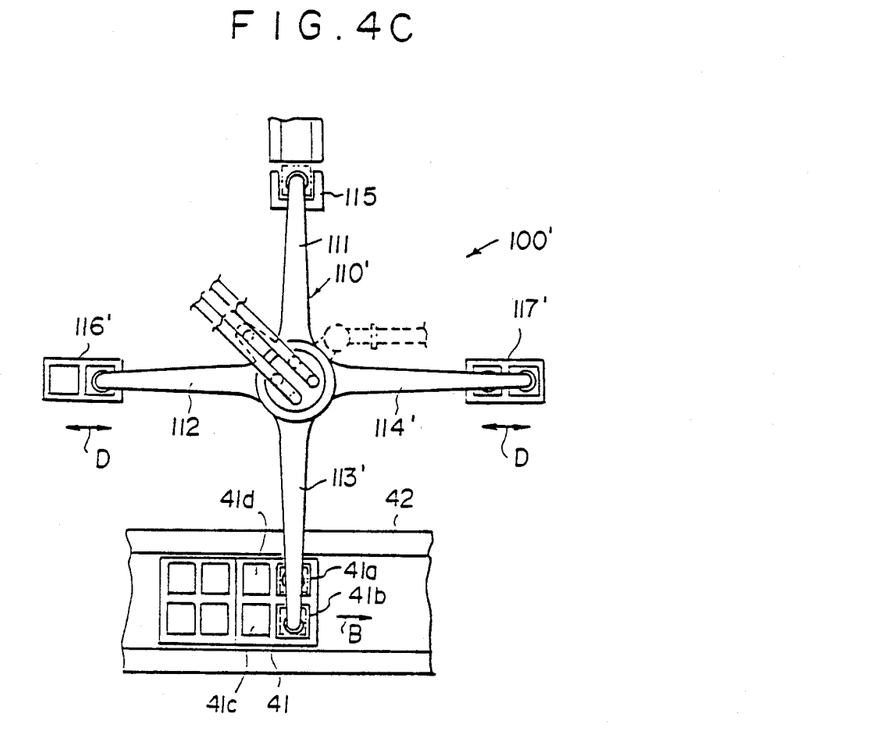
FIG. 4C is a plan view showing a modification of the high speed transfer means.

FIG. 4C shows a high speed transfer means 100' in accordance with another embodiment of the present invention. Since the high speed transfer means 100' of this embodiment is very similar to that of the embodiment shown in FIGS. 4A and 4B, the parts analogous to those shown in FIGS. 4A and 4B are given the same reference numerals and will not be described here. In this embodiment, each of the third and fourth arms 113' and 114' of the rotatable member 110' has a pair of suction cups and each of the first and second arms 111 and 112 has a single suction cup. Each of the second and third tables 116' and 117' is arranged so that a pair of films 4 can be placed thereon side by side. Films 4 fed to the first table 115 are successively transferred to the second and third tables 116' and 117', and the second and third tables 116' and 117' receive the films 4 while being moved back and forth as indicated by arrow D in response to movement of the rotatable members 110' so that a pair of films 4 are placed side by side on each of the second and third tables 116' and 117'. When a pair of films 4 are placed on each of the second and third tables 116' and 117', the films 4 on each of the second and third tables 116' and 117' are simultaneously picked up by the third 113' or the fourth arm 114' and delivered to the pallet 41. In the high speed transfer means 100' of this embodiment, the pallet 41 need only be moved straight along the conveying passage 42.

Figure 5:
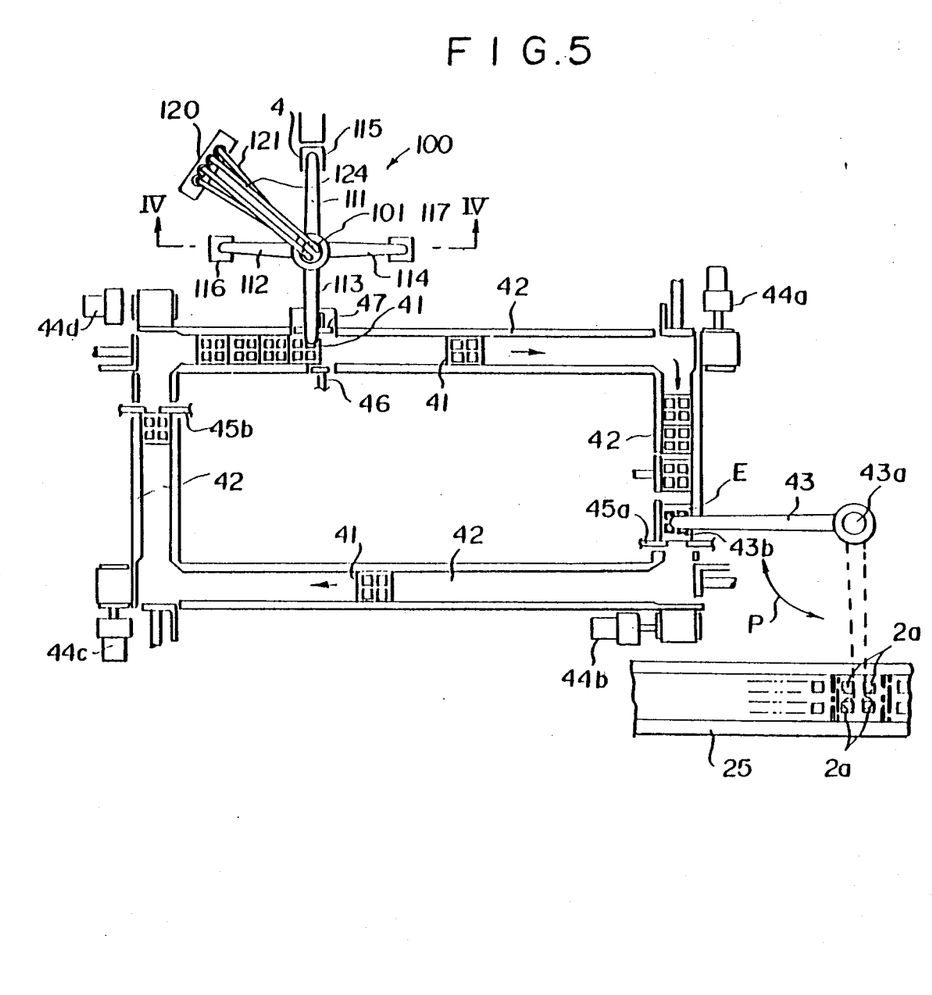
FIG. 5 is a plan view showing the pallet conveying section of the apparatus.

The pallet conveying passage 42 of the passage conveying section 40 is in the form of a rectangular loop as shown in FIG. 5. A plurality of the pallets 41 are placed on a conveyor driven by driving motors 44a to 44d and conveyed along the conveying passage 42 in the clockwise direction. Each pallet 41 has four film receiving portions 41a to 41d each for receiving one chemical analysis film 4 as described above, and when all the film receiving portions 41a to 41d are loaded with the film 4 by the high speed transfer means 100, the pallet 41 is conveyed in the clockwise direction along the passage 42 to position E. A stopper 45a stops the pallet 41 in position E. Above position E, there is provided a sample transfer arm 43 which is rotatable back and forth about a shaft 43a as shown by arrow P and is provided with four suction cups 43b on the free end thereof. The films 4 on the pallet 41 in position E are picked up by the suction cups 43b on the sample transfer arm 43. When the sample transfer arm 43 is rotated to the position shown by the broken line in FIG. 5, the films 14 carried by the suction cups 43b are positioned above the sheet assembly, that is, the first and second sheets 11 and 12 bonded together, on the first conveying passage 25. Then the arm 43 is moved downward and the films 4 are released from the suction cups 43b to be placed in the four chemical analysis film holding openings 2a of a segment of the sheet assembly. Thereafter, the pallet 41 is clockwisely moved along the passage 42 and returned to the original position.

After the chemical analysis film holding openings 2a are thus loaded with the chemical analysis films 4, the sheet assembly is further conveyed along the first conveying passage 25 and the third plastic sheet 13 wound around the third reel 23 is superposed on the sheet assembly on the second sheet side. A second ultrasonic welder 53 (FIGS. 2 and 3) welds the third plastic sheet 13 to the second plastic sheet 12 at portions circumscribing the chemical analysis film holding openings 2a. In this manner, there is formed said sheet assembly 15 (FIG. 1) comprising a plurality of sheet segments connected together with three slits intervening between each pair of sheet segments, each sheet segment including four chemical analysis slides contiguous to each other.

The sheet assembly 15 is further conveyed rightward as seen in FIG. 2 along the first conveying passage 25 to be positioned below a sheet height inspector 70. The sheet height inspector 70 inspects the height of the chemical analysis slides 5 in each sheet segment, thereby inspecting whether the chemical analysis films 4 are correctly loaded in the respective chemical analysis film holding openings 2a. For example, if the third plastic sheet 13 is welded to the second plastic sheet 12 with a part of the film 4 projecting outside the film holding opening 2a, the third plastic sheet 13 bulges out by the thickness of the film 4. Accordingly, by checking whether the third plastic sheet 13 bulges out, it can be checked whether the film 4 is correctly loaded in the film holding opening 2a.

After the sheet height inspection, the sheet assembly 15 is conveyed to be positioned below a film loading inspector 55. The film loading inspector 55 detects whether each chemical analysis film holding opening 2a is loaded with a chemical analysis film 4 by, for instance, detecting whether light can travel through the aligned openings 1a, 2a and 3a without interference.

After checking whether each chemical analysis film holding opening 2a is loaded with the film 4, the sheet assembly 15 is cut along the double dotted chain line shown in FIG. 1 by a stamping press 80, whereby four chemical analysis slides 5 are produced for each sheet segment. In this particular embodiment, the stamping press 80 is of a push-back type and the products or the chemical analysis slides 5 once stamped out from the sheet assembly 15 are returned to the remainder 6 of the sheet assembly 15 to be held thereby. The products thus obtained are conveyed to a product take-out device 90 carried by the remainder 6. The product take-out device 90 separates acceptable products and rejectable products from the products carried by the remainder 6 by first removing the rejectable products from the remainder 6 and subsequently pushing the acceptable products onto a second conveying passage 27. The remainder 6 of the sheet assembly 15 is cut in suitable lengths by a cutter 57 driven by a cylinder 57a and is thrown into a disposal box 29.

Figure 6:
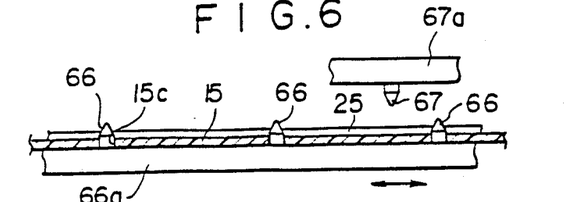
FIGS. 6 and 7 are cross-sectional views for illustrating the operation of a part of the apparatus.
Figure 7:
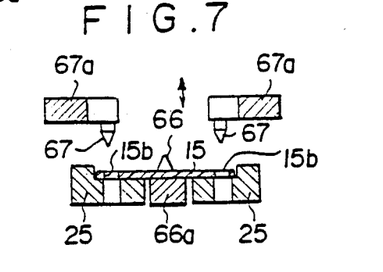

The method of conveying the sheet assembly 15 along the first conveying passage 25 by the feed pins and the method of locating the same in predetermined positions by the locating pins are described with reference to FIGS. 6 and 7, hereinbelow. FIG. 6 is a fragmentary cross-sectional view of a part of the first conveying passage 25 together with the sheet assembly 15 taken along a vertical plane extending in the sheet conveying direction and FIG. 7 is a fragmentary cross-sectional view of the same taken along vertical plane perpendicular to the sheet conveying direction.

A feed pin support 66a is provided at the middle of the first conveying passage 25 for sliding motion in the longitudinal direction of the first conveying passage 25, and a plurality of feed pins 66 are fixed to the feed pin support 66a to project upward at predetermined intervals. The feed pins 66 are respectively engaged with perforations 15c defined by the aligned perforations 11c, 12c and 13c of the sheets 11, 12 and 13. When the feed pin support 66a is moved in the sheet conveying direction, the sheet assembly 25 is conveyed along the first conveying passage 25 by way of engagement of the feed pins 66 with the perforations 15c. Each of the stations at which predetermined operations are performed by ultrasonic welders 51 and 53 and the like is provided, above the first conveying passage 25, with locator pins 67 supported by a locator pin support 67a which is movable up and down. At each station, the feed pin support 66a is moved downward to remove the feed pins 66 away from the perforations 15c, the locator pin support 67a is moved downward onto the sheet assembly 15 to insert the locator pins 67 respectively into locating holes 15b defined by the aligned locating holes 11b, 12b and 13b of the sheets 11, 12 and 13. After the sheet assembly 15 is thus located in each station, the operation to be performed at the station is performed.

The acceptable products 5 pushed onto the second conveying passage 27 by the product take-out device 90 are conveyed along the second conveying passage 27 and transferred to a third conveying passage 28. While the products 5 are conveyed along the third conveying passage 28, predetermined data such as a lot number, date and the like are printed on each product by an ink jet printer 59, and then the print is dried by a drier 61. Then the products are transferred to transfer tables 65 one by one by a transfer arm 63, and further transferred to a depot pallet 69 from the transfer tables 65 by a robot 68 having an arm 68a.

The apparatus of this embodiment is controlled by operating switches 26 disposed on the front side thereof.

We claim:

1. An apparatus for arranging a plurality of sheets side by side in a predetermined pattern on a sheet receiving member comprising means for feeding the sheets to a receiving position one by one, first to fourth rotatable arm members which extend radially from a pivot shaft at intervals of 90°, first to fourth suction means which are respectively mounted on the rotatable arm members and adapted to pick up the sheet under vacuum force, said first to fourth rotatable arm members being rotated together about the pivot shaft alternately counterclockwisely and clockwisely by 90°, the first suction means being adapted to be rotated from the receiving position to a first relay position in response to counterclockwise rotation of the first rotatable arm member to transfer the sheet in the receiving position to the first relay position, and to be rotated from the first relay position to the receiving position in response to clockwise rotation of the same, the second suction means being adapted to be rotated from the first relay position to a delivery position in response to counterclockwise rotation of the second rotatable arm member to transfer the sheet in the first relay position to the delivery position, and to be rotated from the delivery position to the first relay position in response to clockwise rotation of the same, the third suction means being adapted to be rotated from the delivery position to a second relay position in response to counterclockwise rotation of the third rotatable arm member and to be rotated from the second relay position to the delivery position in response to clockwise rotation of the same to transfer the sheet in the second relay position to the delivery position, and the fourth suction means being adapted to be rotated from the second relay position to the receiving position in response to counterclockwise rotation of the fourth rotatable arm member and to be rotated from the receiving position to the second relay position in response to clockwise rotation of the same to transfer the sheet in the receiving position to the second relay position, first to fourth flexible suction hoses for connecting the suction means to a vacuum source, a support means for movably supporting the sheet receiving member in the delivery position, and a drive means for moving the sheet receiving member in synchronization with rotation of the rotatable arm members along a predetermined path corresponding to said predetermined pattern so that a new part of the sheet receiving member is brought to the delivery position each time the sheet receiving member is moved.

2. An apparatus as defined in claim 1 in which said sheets are chemical analysis films obtained by cutting a long chemical analysis film sheet in predetermined lengths, the chemical analysis film sheet comprising a reagent layer and a spreader layer formed on a base film in a continuous length.

3. An apparatus as defined in claim 1 in which said suction means is connected to the flexible suction hose by way of a vacuum passage which is formed through the rotatable arm member to extend near the pivot shaft and is connected to the suction hose at the end near the pivot shaft.

4. A method for individually delivering a plurality of discrete sheets from a receiving position to a delivery position via one of a first or second relay positions by rotating a four-armed member, each of said arms being spaced 90° apart and having a suction device on each end thereof, said receiving position being diametrically opposite said delivery position and said first relay position being diametrically opposite said second relay position, comprising the following steps:

(a) grasping one of said sheets from said receiving position with a first arm of said four-armed member;

(b) rotating said arm member in first direction such that said first arm opposes said first relay position and a second arm opposes said receiving position;

(c) simultaneously releasing said one sheet from said first arm at said first relay position and grasping a second one of said sheets delivered to said receiving position with said second arm;

(d) rotating said arm member in a second direction, opposite to said first direction, such that said first arm opposes said receiving position, said second arm opposes said second relay position and a third arm opposes said first relay position;

(e) simultaneously grasping a third one of said sheets delivered to said receiving position with said first arm, releasing said second sheet from said second arm at said second relay position and grasping said first sheet with said third arm at said first relay position;

(f) rotating said arm in said first direction such that said first arm opposes said first relay position, said second arm opposes said receiving position, said third arm opposes said delivery position and a fourth arm opposes said second relay position;

(g) simultaneously releasing said third sheet from said first arm at said first relay position, grasping a fourth one of said sheets delivered to said receiving position with said second arm, releasing said first sheet from said third arm at said delivery position and grasping said second sheet from said second relay position with said second relay position with said fourth arm; and thereafter;

(h) continuously repeating steps (d) through (g).

5. A method as defined in claim 2 in which said sheets are chemical analysis films obtained by cutting a long chemical analysis film sheet in predetermined lengths, the chemical analysis film sheet comprising a reagent layer and a spreader layer formed on a base film in a continuous length.

* * * * *